(12) United States Patent
Jaakkola et al.

(10) Patent No.: US 10,610,118 B2
(45) Date of Patent: *Apr. 7, 2020

(54) TEXTILE SUBSTRATE FOR MEASURING PHYSICAL QUANTITY

(71) Applicant: Clothing Plus MBU Oy, Kankaanpää (FI)

(72) Inventors: Heikki Jaakkola, Kankaanpää (FI); Tommi Tuulenmäki, Hapuoja (FI); Akseli Reho, Kankaanpää (FI)

(73) Assignee: Clothing Plus MBU Oy, Kankaanpaa (FI)

( * ) Notice: Subject to any disclaimer, the term of this patent is extended or adjusted under 35 U.S.C. 154(b) by 366 days.

This patent is subject to a terminal disclaimer.

(21) Appl. No.: 15/682,080

(22) Filed: Aug. 21, 2017

(65) Prior Publication Data

US 2017/0340231 A1 Nov. 30, 2017

Related U.S. Application Data

(63) Continuation of application No. 13/982,448, filed as application No. PCT/FI2012/050083 on Jan. 31, 2012, now Pat. No. 9,782,096.

(30) Foreign Application Priority Data

Jan. 31, 2011 (FI) ..................... 20115094

(51) Int. Cl.
*A61B 5/0408* (2006.01)
*A61B 5/04* (2006.01)
(Continued)

(52) U.S. Cl.
CPC ........ *A61B 5/04085* (2013.01); *A61B 5/0002* (2013.01); *A61B 5/0245* (2013.01);
(Continued)

(58) Field of Classification Search
CPC . A61B 5/04085; A61B 5/6804; A61B 5/6805; A61B 5/6806; A61B 5/6807; A61B 5/681
See application file for complete search history.

(56) References Cited

U.S. PATENT DOCUMENTS 3,479,565 A 11/1969 Ross et al.
3,631,298 A 12/1971 Davis
(Continued)

FOREIGN PATENT DOCUMENTS

CH 662717 A5 10/1987
CN 200966186 Y 10/2007
(Continued)

OTHER PUBLICATIONS

Swedberg, Claire, "Fulfillment Efficiency With RFID", RFID Journal, Nov. 10, 2011, pp. 1-4, http://www.rfidjournal.com/article/view/8953.

*Primary Examiner* — Lee S Cohen
(74) *Attorney, Agent, or Firm* — Young Basile Hanlon & MacFarlane, P.C.

(57) ABSTRACT

A textile substrate with a measuring sensor for measuring a physiological signal. The textile substrate has integrated irremovably therewith a base structure component for electronics, such as for example a plastic base for a transmitter for attaching the transmitter and other electronics to the substrate irremovably by way of said base structure component. In addition, signal transfer elements from the measuring sensor are adapted to extend in a watertight manner to the electronics through said base structure component integrated irremovably with the textile substrate.

18 Claims, 2 Drawing Sheets

(51) Int. Cl.
*A61B 5/00* (2006.01)
*H01R 13/52* (2006.01)
*A61B 5/024* (2006.01)
*A61B 5/0245* (2006.01)

(52) U.S. Cl.
CPC ............ *A61B 5/02438* (2013.01); *A61B 5/04* (2013.01); *A61B 5/0408* (2013.01); *A61B 5/6804* (2013.01); *A61B 5/6807* (2013.01); *H01R 13/5213* (2013.01); *Y10T 29/49002* (2015.01)

(56) References Cited

U.S. PATENT DOCUMENTS

| | | | |
|---|---|---|---|
| 3,954,100 | A | 5/1976 | Sem-Jacobsen |
| 4,729,377 | A | 3/1988 | Granek et al. |
| 4,763,660 | A | 8/1988 | Kroll et al. |
| 5,450,845 | A | 9/1995 | Axelgaard |
| 5,624,736 | A | 4/1997 | DeAngelis et al. |
| 6,047,203 | A | 4/2000 | Sackner et al. |
| 6,080,690 | A | 6/2000 | Lebby et al. |
| 6,145,551 | A | 11/2000 | Jayaraman et al. |
| 6,210,771 | B1 | 4/2001 | Post et al. |
| 6,368,990 | B1 | 4/2002 | Jennergren et al. |
| 6,381,482 | B1 | 4/2002 | Jayaraman et al. |
| 6,400,975 | B1 | 6/2002 | McFee |
| 6,501,055 | B2 | 12/2002 | Rock et al. |
| 6,729,025 | B2 | 5/2004 | Farrell et al. |
| 6,941,775 | B2 | 9/2005 | Sharma |
| 7,206,630 | B1 | 4/2007 | Tarler |
| 7,559,902 | B2 | 7/2009 | Ting et al. |
| 7,712,373 | B2 | 5/2010 | Nagle et al. |
| 8,003,887 | B1 | 8/2011 | Hsieh et al. |
| 8,224,418 | B2 | 7/2012 | Birnbaum et al. |
| 8,750,959 | B2 | 6/2014 | Lindberg et al. |
| 9,782,096 | B2 * | 10/2017 | Jaakkola ................ A61B 5/04 |
| 2002/0026112 | A1 | 2/2002 | Nissila et al. |
| 2002/0076948 | A1 | 6/2002 | Farrell et al. |
| 2002/0082491 | A1 | 6/2002 | Nissila |
| 2002/0124295 | A1 | 9/2002 | Fenwick et al. |
| 2002/0154518 | A1 | 10/2002 | Elferich |
| 2003/0224685 | A1 | 12/2003 | Sharma |
| 2005/0054941 | A1 | 3/2005 | Ting et al. |
| 2005/0275416 | A1 | 12/2005 | Hervieux et al. |
| 2006/0124193 | A1 | 6/2006 | Orr et al. |
| 2006/0152377 | A1 | 7/2006 | Beebe et al. |
| 2006/0224072 | A1 | 10/2006 | Shennib |
| 2006/0267790 | A1 | 11/2006 | Matthiessen et al. |
| 2007/0073131 | A1 | 3/2007 | Ryu et al. |
| 2007/0083096 | A1 | 4/2007 | Paradiso |
| 2007/0177298 | A1 | 8/2007 | Jaatinen et al. |
| 2007/0285868 | A1 | 12/2007 | Lindberg et al. |
| 2007/0298666 | A1 | 12/2007 | Kurth |
| 2008/0208029 | A1 | 8/2008 | Thijs et al. |
| 2008/0287770 | A1 | 11/2008 | Kurzweil et al. |
| 2009/0018428 | A1 | 1/2009 | Dias et al. |
| 2009/0112079 | A1 | 4/2009 | Hassonjee et al. |
| 2009/0173529 | A1 | 7/2009 | Lee et al. |
| 2009/0281394 | A1 | 11/2009 | Russell et al. |
| 2010/0198043 | A1 | 8/2010 | Holzer et al. |
| 2010/0298899 | A1 | 11/2010 | Donnelly et al. |
| 2011/0160601 | A1 | 6/2011 | Wang et al. |
| 2011/0213208 | A1 | 9/2011 | McKenna et al. |
| 2011/0282164 | A1 | 11/2011 | Yang et al. |
| 2013/0085538 | A1 | 4/2013 | Volpe et al. |
| 2013/0160183 | A1 | 6/2013 | Reho et al. |
| 2013/0274587 | A1 | 10/2013 | Coza et al. |
| 2013/0281795 | A1 | 10/2013 | Varadan |
| 2013/0321168 | A1 | 12/2013 | Mahony et al. |
| 2014/0015410 | A1 | 1/2014 | Shibata et al. |
| 2014/0070957 | A1 | 3/2014 | Longinotti-Buitoni |
| 2014/0090146 | A1 | 4/2014 | Yeomans et al. |
| 2014/0275883 | A1 | 9/2014 | Haisley et al. |
| 2014/0318699 | A1 | 10/2014 | Longinotti-Buitoni |
| 2014/0343392 | A1 | 11/2014 | Yang |
| 2015/0025354 | A1 | 1/2015 | Salonius et al. |
| 2016/0038083 | A1 | 2/2016 | Ding |

FOREIGN PATENT DOCUMENTS

| | | |
|---|---|---|
| CN | 201114998 Y | 9/2008 |
| DE | 10338029 A1 | 4/2005 |
| DE | 102004058731 A1 | 6/2006 |
| EP | 0509689 A2 | 10/1992 |
| EP | 0855167 A1 | 7/1998 |
| EP | 0947967 A1 | 10/1999 |
| EP | 1095612 A1 | 5/2001 |
| EP | 1504739 A1 | 2/2005 |
| EP | 1632926 A1 | 3/2006 |
| EP | 1676528 A1 | 7/2006 |
| EP | 1894523 A1 | 3/2008 |
| EP | 2057943 A1 | 5/2009 |
| EP | 2082967 A1 | 7/2009 |
| EP | 2975915 A1 | 1/2016 |
| FI | 119456 B | 11/2008 |
| FI | 119716 B | 2/2009 |
| GB | 2257523 A | 1/1993 |
| GB | 2503716 A | 1/2014 |
| JP | 2015-083045 A2 | 4/2015 |
| KR | 2012-0009000 A | 2/2012 |
| WO | 99/64657 A2 | 12/1999 |
| WO | 00/19957 A1 | 4/2000 |
| WO | 00/44411 A1 | 8/2000 |
| WO | 01/01855 A1 | 1/2001 |
| WO | 01/02052 A2 | 1/2001 |
| WO | 01/34886 A1 | 5/2001 |
| WO | 01/48291 A1 | 7/2001 |
| WO | 01/49912 A1 | 7/2001 |
| WO | 01/78577 A2 | 10/2001 |
| WO | 02/30279 A1 | 4/2002 |
| WO | 02/032665 A1 | 4/2002 |
| WO | 02/40091 A2 | 5/2002 |
| WO | 02/071935 A1 | 9/2002 |
| WO | 02/098659 A1 | 12/2002 |
| WO | 03/010561 A2 | 2/2003 |
| WO | 2004/086968 A1 | 10/2004 |
| WO | 2006/029105 A2 | 3/2006 |
| WO | 2006/068811 A1 | 6/2006 |
| WO | 2006/094152 A2 | 9/2006 |
| WO | 2006/128957 A1 | 12/2006 |
| WO | 2006/129272 A2 | 12/2006 |
| WO | 2007/050650 A2 | 5/2007 |
| WO | 2007/107906 A1 | 9/2007 |
| WO | 2008/071843 A1 | 6/2008 |
| WO | 2009/107906 A1 | 9/2009 |
| WO | 2012/176193 A1 | 12/2012 |
| WO | 2013/033238 A1 | 3/2013 |
| WO | 2015/136521 A1 | 9/2015 |

* cited by examiner

TEXTILE SUBSTRATE FOR MEASURING PHYSICAL QUANTITY

CROSS REFERENCE TO RELATED APPLICATIONS

This application is a continuation of U.S. patent application Ser. No. 13/982,448, filed Oct. 8, 2013, now U.S. Pat. No. 9,782,096, issued on Oct. 10, 2017, which claims the benefit of National Phase entry of PCT Application No. PCT/FI2012/050083, filed Jan. 31, 2012, and of Finland Application No. 20115094, filed Jan. 31, 2011, the disclosures of which are hereby incorporated by referenced herein in their entirety.

FIELD OF INVENTION

The present invention relates to a textile substrate for measuring a physical quantity. The present invention is particularly related to a textile sensor substrate, wherein the textile substrate comprises a measuring sensor, such as for example electrodes, for measuring a physiological signal.

BACKGROUND

The prior art discloses various solutions with a sensor for measuring a physical quantity, such as for example a heart rate band or belt. The heart rate band is made of skin contacting electrodes, and electronics which identifies a signal emanating from the electrodes and transmits the received heart rate data to a terminal, for example to a watch or a mobile communicator. For conducting a measurement, the heart rate band is put on for example around the thorax, whereby the electrodes make contact with the skin around the chest close to the heart for a measuring process.

For example, publication FI 119456 discloses one heart rate belt with a sensor, wherein the heart rate belt has its sensor in a first part of a connector mechanism and has its processing or transmitter unit in a second part of the connector mechanism. Both parts include magnetic layers, by means of which the parts connect releasably to each other by way of mechanical coupling. In the solution, the electrical conductor layers extending from the sensor are connected electrically with the second part electrical components of the processing or transmitter unit as a result of the aforesaid mechanical coupling.

In addition, publication FI 119716 discloses a heart rate measuring arrangement comprising a band-like structural component, wherein the structural component, in terms of its material, is flexible, soft, and closely fitting to the skin surface, such as for example a band-aid type adhesive tape. The arrangement includes an electronic unit in electrical communication with heart rate measuring electrodes. The unit is arranged in a casing which comprises a gripping means for attaching the unit to the band-like component of the electrode structure, such that the gripping means provide an electrical connection between the electrodes and the electronic unit. The gripping means is for example an attachment slot, a pivoted clamping clip or the like.

The prior art measuring arrangements are typically all plastic or rubber in structure, wherein for example the measuring band is fabricated with injection molding technology by pressing the conducting plastic electrodes, plastic insulations and electronics within the structure.

The prior art solutions nevertheless involve certain problems. Plastic bands are cold, among other things, and the hard and cold presence thereof does not feel comfortable on the skin. Therefore, recent newcomers to the marketplace include also heart rate measuring bands made partially of textile. On the other hand, a problem with partially textile bands is that the manufacturing processes of textile and those of plastics as well as those of electronics are clearly different from each other in terms of character and technology, which is why the textile sensor band, and electrodes integrated therewith, must be manufactured in a separate process and, respectively, the transmitter module must be manufactured in a separate process. A particular problem here is due to the fact that, in order to achieve a final product or, in other words, in order to bond a textile band and electronics to each other, it is absolutely necessary to provide therebetween a mechanically and electrically reliable connection, by which connection an electrical measurement signal can be delivered from the skin and sensors to the electronics. Since the measurement signal is highly sensitive to interferences and the environment is particularly demanding (sweaty and with motion disturbances), the connection is subject to quite high qualifications. In addition to communicating the signal, the connection is required, among other things, to retain the transmitter module mechanically immobile in attachment with a textile band. Coming up with sufficiently reliable bonding technique between a textile band and electronics is nevertheless quite expensive considering the final product.

It is a rough estimate that the price of a plastic heart rate band, having electronics integrated as a part of the plastic band, is only about 60% of that of a separate textile band and a transmitter attached thereto with prior art technology. The most significant cost factor is the necessary bonding technology between a textile band and a plastic transmitter. In most commercial solutions, the bonding technique between a band and a transmitter is typically implemented with snap fasteners.

SUMMARY

One objective of the present invention is to eliminate or at least to alleviate drawbacks related to the prior art. According to one embodiment, the present invention pursues to provide such a textile substrate for measuring a physiological signal, wherein the expensive bonding technique of the prior art could be relinquished and wherein the motion disturbance-hampered and moist environment would not be able to cause interference in the sensitive measurement signal. In addition, the present invention pursues to make it possible, among other things, that the manufacturing processes of textiles as well as those of electronics could still be maintained separate from each other whenever necessary for thereby taking advantage of the characteristic features and knowledge of both industries. It is a particular objective of the present invention to enable the integration of textile and electronics quickly, conveniently, cost efficiently and with functional reliability for providing a reliable product.

Some objectives of the present invention are accomplished for example with a textile substrate.

In some aspects, the textile substrate of the present invention comprises a measuring sensor for measuring a physiological signal, wherein the textile substrate is provided with a region having irremovably integrated therewith a structure more rigid than the textile substrate structure for the attachment of electronics to said region irremovably by way of said more rigid structure, and signal transfer elements being adapted to be connected across said region to the electronics in a watertight manner.

In some aspects, a method for manufacturing a textile substrate of the present invention comprises providing the textile substrate with measuring sensors for measuring a physiological signal, wherein the method further comprises providing the textile substrate with a region, with said region being irremovably integrated a structure more rigid than the textile substrate structure for the attachment of electronics irremovably to said region by way of said more rigid structure, and signal transfer elements being adapted to be connected from the measuring sensors across said region to the electronics in a watertight manner.

In some aspects, a wearable article of the present invention comprises a heart rate belt or band, or a garment, for example a shirt, a bra, a sports accessory, an undergarment, a sock, or a pair of pants, wherein the wearable article comprises a textile substrate, wherein said textile substrate comprises a measuring sensor for measuring a physiological signal, wherein the textile substrate is provided with a region, said region having irremovably integrated therewith a structure more rigid than the textile substrate structure for the attachment of electronics to said region irremovably by way of said more rigid structure, and signal transfer elements being adapted to be connected across said region to the electronics in a watertight manner.

According to one embodiment of the present invention, the textile substrate comprises a measuring sensor for measuring a physiological signal. The sensor is most preferably implemented with appropriate electrodes for measuring a physiological signal, such as for measuring for example heart rate, respiratory rate, oxygen saturation, temperature, ECG, EEG, or electrical impedance. In the present invention, the textile substrate is preferably provided with a region for the attachment of electronics, such as a transmitter, to the substrate across said region in an irremovable manner. In addition, signal transfer elements from the measuring sensor are adapted to be connected to the electronics by way of said region in a watertight manner.

According to one preferred embodiment, said region has irremovably integrated therewith a structure, most preferably as early as concurrently with manufacturing the substrate, which structure is more rigid than the textile substrate structure, and to which the electronics, for example a wireless transmitter and measurement data processing electronics, can be attached in an irremovable manner. According to a particularly preferred embodiment, said more rigid structure is a base structure, for example a plastic base for electronics, for example a transmitter. In this case, the actual textile component can be manufactured separately and, concurrently with its manufacturing process, with said textile component can be integrated for example a plastic base for the transmitter, and the plastic base can be provided with signal transfer conductors extending from the electrodes. Respectively, in connection with assembling the final product, the electronics will be attached to the base structure irremovably as described elsewhere in this document.

This offers obvious benefits over the prior art solutions, because thereby e.g. the manufacturing processes of textiles as well as those of electronics can still be maintained separate from each other, and hence advantage can be taken of the characteristic features and knowledge of both industries. The present invention enables for example the integration of a transmitter as a textile band component during textile manufacturing across a plastic base integrated therewith at any manufacturing stage of the band after the plastic base has been integrated with the textile.

Most preferably, said base structure for a transmitter is, in terms of its mechanical design, such that it functions as a mechanical mating component for the transmitter (or other possible electronics), thus enabling the transmitter to be attached as a mating component of the base structure irremovably to said textile substrate by way of the base structure. The attachment can be implemented or secured not only by mating component technique but also, among other means, by injection molding, gluing, sewing, screws, upsetting, ultrasonic welding, and/or by high frequency or heat lamination. In addition, the base structure is attached to the textile substrate most preferably for example by injection molding, gluing, sewing, screws, upsetting, ultrasonic welding, and/or by high frequency or heat lamination. The measurement signal is conducted from electrodes to electronics most preferably by signal transfer elements implemented with conductors. According to one embodiment of the present invention, the conductors connect from the textile substrate across said region, or a rigid structure irremovably integrated therewith, such as for example across the plastic base of a transmitter, to the electronics by way of watertight penetrations or other watertight arrangements in an electrical fashion. According to one preferred embodiment, the conductors extend to the electronics directly through the plastic base in a water tight manner without any separate elements. It is also possible that the plastic base of a transmitter be provided with signal transfer elements, for example pins, by way of which the signal is adapted to proceed from conductors to electronics in an electrical manner. When electronics is attached to a plastic base irremovably as described in this document, the plastic base and the electronics in attachment therewith establish one integral assembly and for example perspiration is not able to cause problems or disruptions for electrical connections between signal transfer conductors and electronics.

According to one embodiment of the present invention, on top of the transmitter or other electronics is provided a second component structurally more rigid than the textile substrate structure, such as for example a protective cover for protecting the transmitter and other electronics at least mechanically, whereby the protective cover, jointly with the base component, makes up an enclosure for the transmitter and other electronics, as well as for a battery. It should be noted that between said substrate and the second component placed on top of the electronics exists just a mechanical connection, but no electrical connections. According to one embodiment, said second component, for example a protective cover, is designed to be removable for enabling a battery replacement, for example. Furthermore, said second component can be at least partially coated with textile.

The present invention offers obvious benefits over the prior art. For example, in the fixed integration of a transmitter's base and a textile component, for example a textile band for the heart rate belt, there is achieved not only the avoidance of expensive technology but at the same time also a watertight and durable penetration of electrodes or signal transfer conductors into the transmitter enclosure. The transmitter's base structure integrated with the textile component provides a natural location for transmitter electronics. This plastic interface provides a surface to which all current plastics and electronics manufacturers will be able to attach their particular electronics. The enclosure is closed most preferably with a transmitter's cover, which, according to one embodiment, can be openable for example for a battery replacement. What is essential, however, is that there are no electrical signals traveling between the openable cover (the second component set on top of said substrate and the electronics) and the base. Accordingly, the cover only functions as a seldom operated battery replacement opening. In case the battery replacement is not desirable, the cover can be for example welded permanently to the attachment with the transmitter's base, whereby the electronics is encapsulated for a permanent component of the band.

BRIEF DESCRIPTION OF THE DRAWINGS

Preferred embodiments of the invention will be described in the next section a little more precisely with reference to the accompanying figures, in which.

DETAILED DESCRIPTION OF THE PREFERRED EMBODIMENTS

Figure 1:
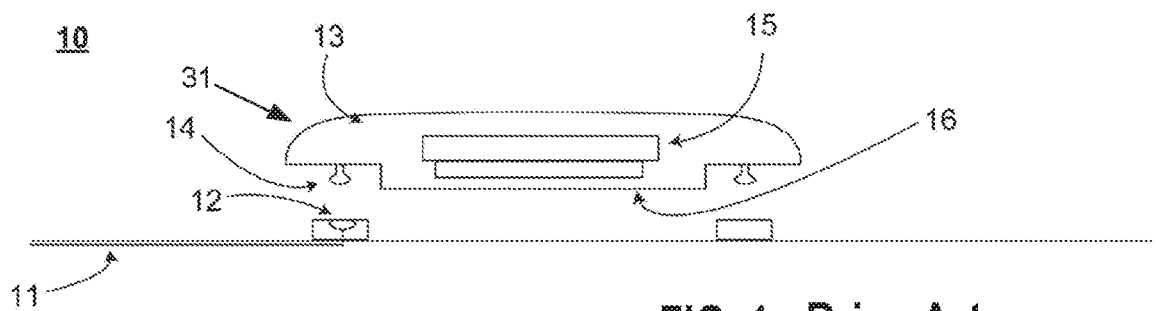
FIG. 1 shows one typical heart rate band of the prior art.

FIG. 1 shows one typical heart rate band 10 of the prior art, wherein from a skin contacting sensor extends a conductor 11 to a connection 12 present in the band, whereby a transmitter module 13 is connected in an electrically and mechanically releasable manner by way of a connection 14 present in the transmitter module. The connection is most typically implemented as a snap fastener type coupling. The transmitter module 13, which is releasably attachable to the band by means of a snap fastener type coupling, comprises generally also electronics 15 and a battery 16. The battery 16 is typically located at the bottom of the transmitter module 13 for a convenient replacement by releasing the module from the sensor band's connector mechanisms 12. In the prior art solution, for example perspiration has an easy access into a connection implemented with snap fasteners, thus being likely to cause interference in the measurement signal along with vibration.

Figure 2:
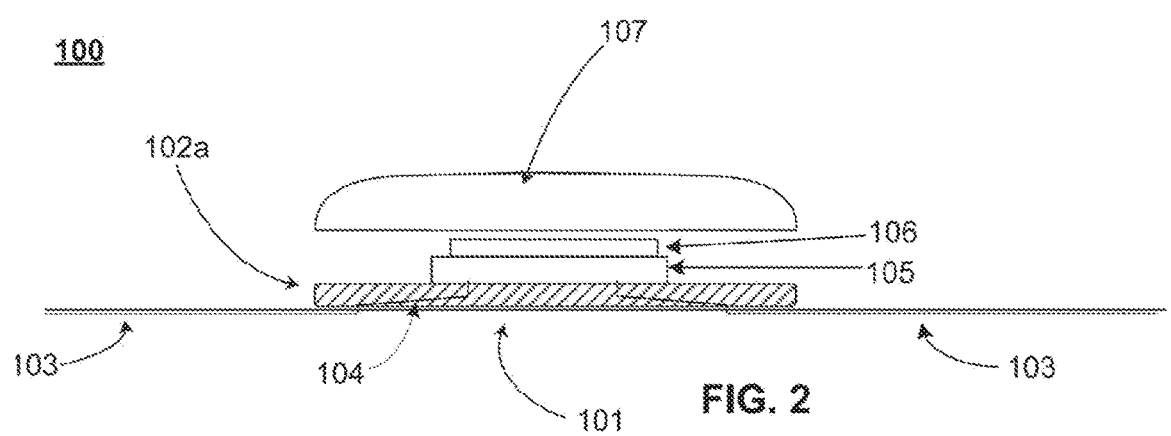
FIG. 2 shows one exemplary heart rate band according to one preferred embodiment of the present invention.

FIG. 2 shows one exemplary heart rate band 100 according to one preferred embodiment of the present invention, wherein a body component of the heart rate band is established by a textile sensor substrate 101, which is provided with a region 102a for the attachment of electronics to the substrate across said region 102a in an irremovable manner. It is also across said region 102a that signal transfer elements 103 extending from a measuring sensor are adapted to connect to the electronics in a watertight manner. The region 102a can be designed for example in such a manner that, when placed thereon, the electronics can be attached to the region and thereby to the textile substrate irremovably for example with a technique described elsewhere in this document.

In the heart rate band depicted in FIG. 2, the conductors 103 are adapted to extend most preferably from the textile substrate 101 through said region 102a directly 104 to the electronics 105. Said irremovably attached electronics 105 comprises most preferably at least a transmitter for the wireless transmission of measured signals. The electronics may further comprise also elements for processing measurement signals.

In the heart rate band 100, on top of said region 102a and the electronics 105 as well as the battery 106 is most preferably provided a cover 107, whereby the cover 107, jointly with said region 102a, makes up an enclosure type member for protecting the electronics and the battery mechanically. The enclosure can be openable for an easy replacement of the battery which lies on top.

Figure 3:
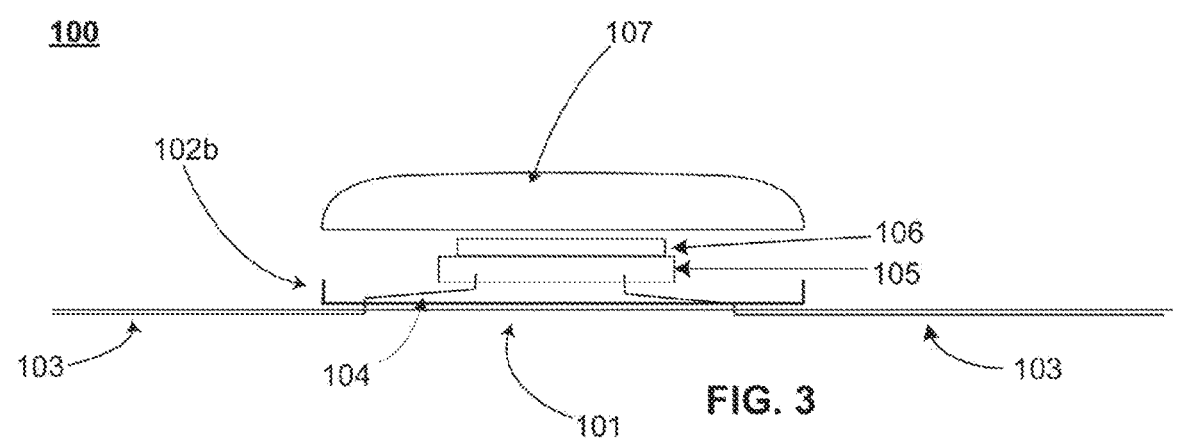
FIG. 3 shows another exemplary heart rate band according to one preferred embodiment of the present invention.
Figure 4:
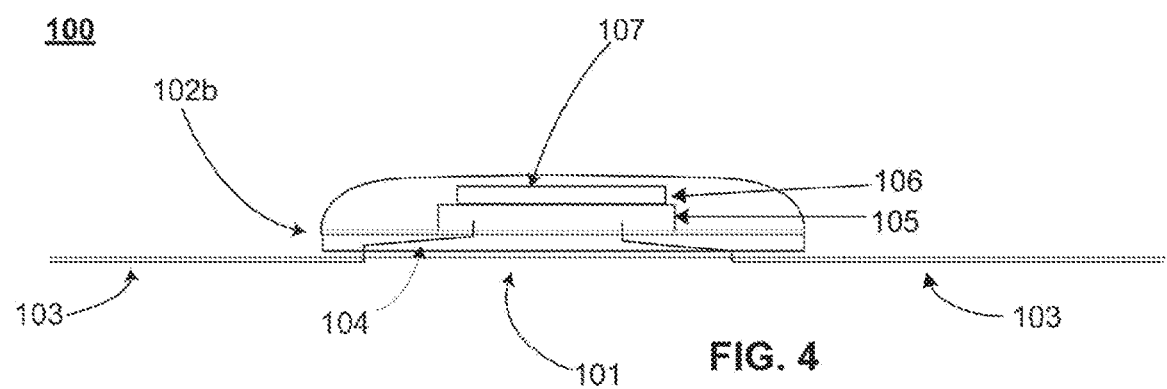
FIG. 4 shows one exemplary heart rate band in a closed condition according to one preferred embodiment of the present invention.

FIG. 3 depicts another exemplary heart rate band 100 according to one preferred embodiment of the present invention, which is structurally highly similar to that shown in FIG. 2, and reference numbering for the like elements is consistent with that of FIG. 2. With regard to a textile substrate 101 in FIG. 3, the textile substrate has irremovably integrated therewith a base structure 102b for electronics, such as for example a plastic transmitter base, with a transmitter 105 attached irremovably thereto. On top of the transmitter (and other possible electronics) 105 is most preferably provided a battery 106. Similarly, the heart rate band depicted in FIG. 3 has conductors 103 adapted to extend most preferably from the textile substrate 101 through said transmitter's base structure 102b directly 104 to the electronics 105, thus providing at the same time a watertight and mechanically durable penetration through the base structure 102b. In addition, adapted to be placed on top of the electronics and the battery is a cover 107, which can be designed to be openable for enabling a battery replacement. According to one embodiment, the cover can be adapted to become attached to the transmitter's base structure 102b as presented in FIG. 4. According to one embodiment, the cover can be coated with textile.

Figure 5:
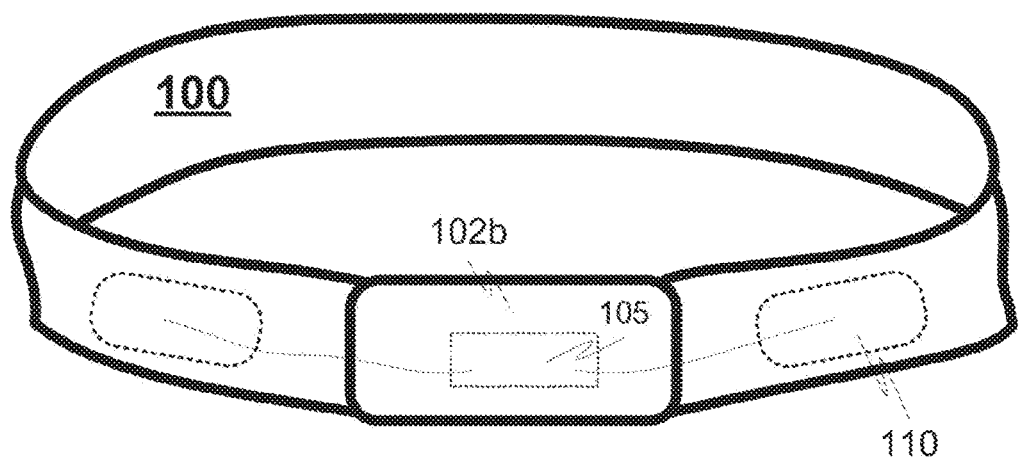
FIG. 5 shows an example of a wearable article according to the present invention.
Figure 6:
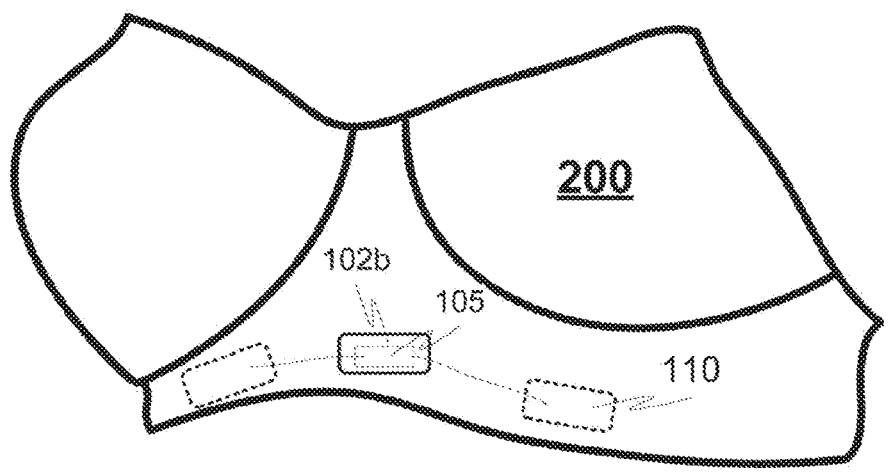
FIG. 6 shows an example of a wearable article according to the present invention.
Figure 7:
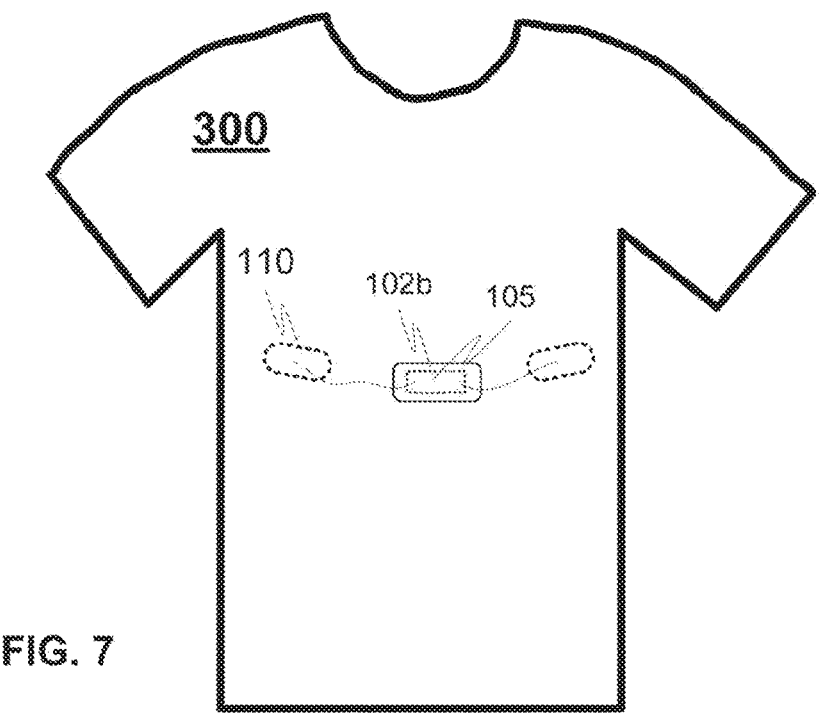
FIG. 7 shows an example of a wearable article according to the present invention.

FIGS. 5, 6 and 7 illustrate a few examples of wearable articles 100, 200, 300 of the present invention, wherein, depending on the wearable article, sensors 110 made up by electrodes are placed in an appropriate location for measuring a desired physical quantity, such as, for example, close to the heart in a bra 200 and a shirt 300 for measuring the heart rate.

The foregoing are just a few embodiments of the present invention. The principle according to the present invention can naturally be varied within the scope of protection defined by the claims, regarding for example implementation details and fields of use. It should particularly be noted that, although the above description deals with a heart rate band or belt as one example of a textile substrate, the present invention is by no means limited solely to those, but said textile substrate can also be some other wearable article or garment, such as for example a shirt, a bra, a sports accessory, an undergarment, a sock, or a pair of pants. In addition, although it has been stated in several examples that the textile substrate has irremovably integrated therewith a plastic base for electronics, such as for a transmitter, the material of said base structure may just as well be a material other than plastics.

What is claimed is:

1. A device including a textile substrate, comprising:
    a base structure including electronics and at least one signal transfer element connected to the electronics, the base structure being irremovably and permanently integrated into the textile substrate;
    at least one sensor; and
    at least one signal transfer conductor connected to the at least one sensor and connected to the at least one signal transfer element, the at least one signal transfer conductor extended from the at least one sensor along the textile substrate;
    wherein the at least one signal transfer element and the at least one signal transfer conductor enable signal transfer in an irremovably, permanently integrated and watertight manner between the at least one sensor and the electronics.

2. The device of claim 1, wherein the at least one sensor includes at least one electrode, the at least one electrode being connected to the at least one signal transfer conductor.

3. The device of claim 1, wherein the electronics includes at least a transmitter for wireless transmission of measured signals.

4. The device of claim 1, further comprising:
a cover mechanically connected to a top of the base structure.

5. The device of claim 4, wherein the cover is removable.

6. The device of claim 5, wherein the cover is at least partially coated with a textile.

7. The device of claim 1, wherein the textile substrate is a heart rate belt, a band, or a garment.

8. The device of claim 1, wherein the textile substrate is a wearable article.

9. The device of claim 8, wherein the wearable article is a garment selected from the group consisting of a shirt, a bra, a sports accessory, an undergarment, a sock or a pair of pants.

10. A method for manufacturing a device, the method comprising:
providing a textile substrate;
providing a base structure including electronics and at least one signal transfer element connected to the electronics, the base structure being irremovably and permanently integrated into the textile substrate;
providing at least one sensor; and
providing at least one signal transfer conductor along the textile substrate;
connecting the at least one signal transfer conductor to the at least one sensor and to the at least one signal transfer element,
wherein the at least one signal transfer element and the at least one signal transfer conductor enable signal transfer in an irremovably, permanently integrated and watertight manner between the at least one sensor and the electronics.

11. The method of claim 10, further comprising:
providing a cover; and
mechanically connecting the cover to a top of the base structure.

12. The method of claim 11, wherein the cover is removable.

13. The method of claim 12, wherein the cover is at least partially coated with a textile.

14. The method of claim 10, wherein the at least one sensor includes at least one electrode, further comprising:
connecting the at least one electrode to the at least one signal transfer conductor.

15. The method of claim 10, wherein the electronics includes at least a transmitter for wireless transmission of measured signals.

16. The method of claim 10, wherein the textile substrate is a heart rate belt, a band, or a garment.

17. The method of claim 16, wherein the textile substrate is a wearable article.

18. The method of claim 17, wherein the wearable article is a garment selected from the group consisting of a shirt, a bra, a sports accessory, an undergarment, a sock or a pair of pants.

* * * * *